United States Patent [19]

Loertscher

[11] Patent Number: 5,151,098
[45] Date of Patent: Sep. 29, 1992

[54] APPARATUS FOR CONTROLLED TISSUE ABLATION

[76] Inventor: Hanspeter Loertscher, Zedtwitzweg 2, CH-3626, Hunibach, Switzerland

[21] Appl. No.: 675,442

[22] Filed: Mar. 26, 1991

Related U.S. Application Data

[63] Continuation-in-part of Ser. No. 556,900, Jul. 23, 1990, abandoned.

[51] Int. Cl.$^5$ .............................................. A61B 17/36
[52] U.S. Cl. .......................................... 606/16; 606/19
[58] Field of Search ............................... 128/395-398; 606/13-16, 3

[56] References Cited

U.S. PATENT DOCUMENTS

| | | | |
|---|---|---|---|
| 4,122,853 | 10/1978 | Smith | 606/19 |
| 4,273,109 | 6/1981 | Enderby | 606/16 |
| 4,385,832 | 5/1983 | Doi et al. | 606/16 |
| 4,693,244 | 9/1987 | Daikuzono | 606/16 |
| 4,806,289 | 2/1989 | Laursen et al. | 350/96.32 |
| 4,819,632 | 4/1989 | Davies | 606/15 |
| 4,846,172 | 7/1989 | Berlin | 128/395 |
| 4,878,492 | 11/1989 | Sinofsky et al. | 606/13 |

OTHER PUBLICATIONS

Article: Krokhin ON: *Generation of High-Temperature Vapors and Plasma by Laser Radiation* In Arecchi FT, Laser Handbook, vol. 2. Amsterdam, North Holland, 1972, pp. 1371-1407.

*Primary Examiner*—Max Hindenburg
*Attorney, Agent, or Firm*—Hopkins & Thomas

[57] ABSTRACT

An apparatus for performing controlled tissue ablation in endolaser microsurgery is disclosed, the apparatus including a laser delivery system coupled to a probe capable of transmitting the laser power through a suitable medium such as sapphire. The probe may include a central canal for aspiration and irrigation and delivers a cross-sectionally homogeneous power distribution. The apparatus is designed to control the ablation depth and to limit the zone of thermal damage in the remaining tissue.

20 Claims, 3 Drawing Sheets

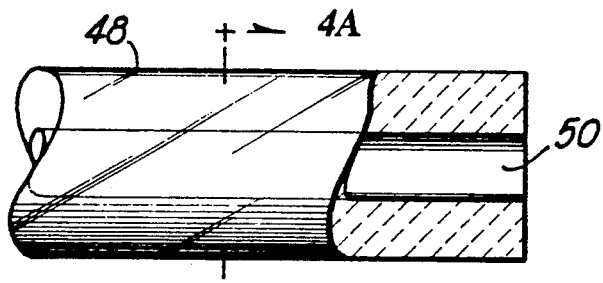 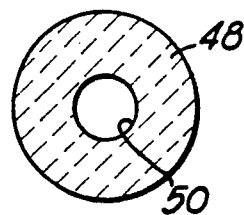
FIG 4    FIG 4A
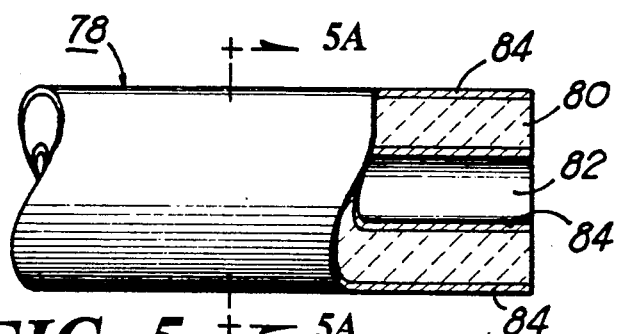 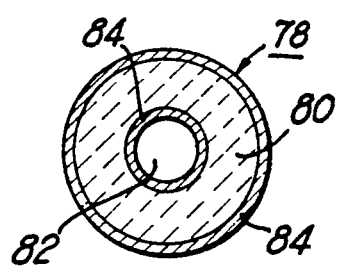
FIG 5    FIG 5A
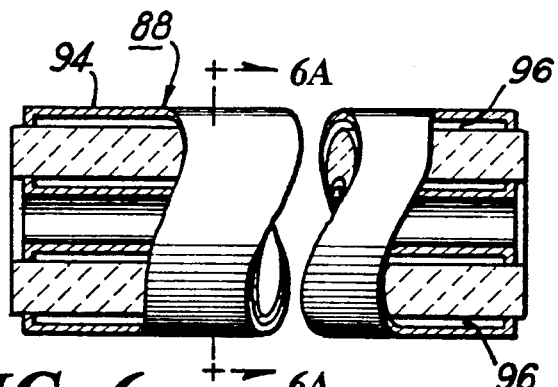 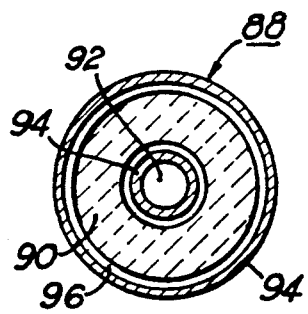
FIG 6    FIG 6A
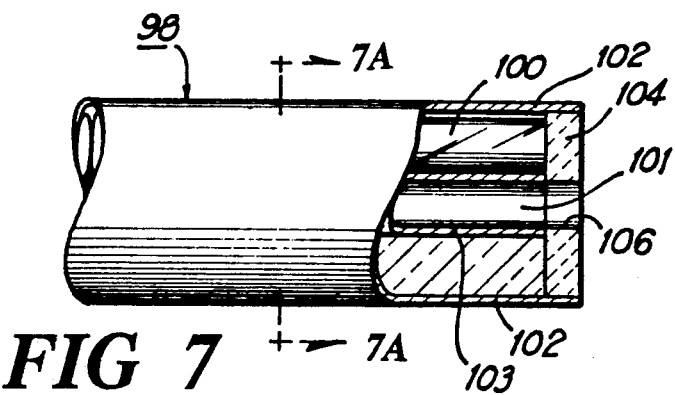 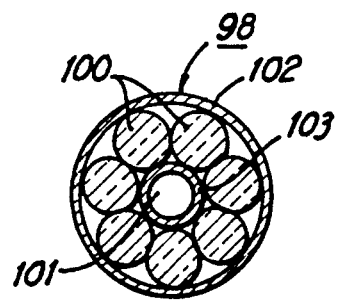
FIG 7    FIG 7A

APPARATUS FOR CONTROLLED TISSUE ABLATION

This application is a continuation-in-part of application Ser. No. 556,900, filed Jul. 23, 1990, now abandoned.

BACKGROUND OF THE INVENTION

Various mechanical instruments have been devised for microsurgery, such as in eye surgery, where the removal of the gel-like vitreous and associated membranes is a difficult and delicate task in the treatment of vitreoretinal diseases. Other microsurgical procedures include the formation of a new drainage fistula in the sclera of glaucoma patients to relieve the intraocular pressure, removal of lens material in cataract surgery, removal of masses from herniated discs in back surgery, and the partial removal of soft tissues in joint and brain surgery. The inherent disadvantages of the mechanical devices are caused by the frictions of the movements necessary for cutting and the traction and shearing forces exerted upon adjacent tissues. Such mechanical disturbances of delicate structures often result in excessive scarring, which can reduce or even eliminate the benefit of the operation, or which can delay the healing process.

Recent advances in technology and techniques have made the use of lasers in surgical procedures increasingly common. The precision attained through the use of lasers and laser equipment has particular advantages in microsurgical procedures which were formerly either not possible, or more traumatic using conventional instruments. As the field has developed, however, some of the techniques which are now in use and which are theoretically sound have led to previously unforeseen problems.

The pulsed mid-infrared lasers, such as Thulium (1.96 um wavelength, 100 um penetration depth in water), Holmium (2.1 um, 300 um penetration depth), and Erbium:YAG (2.94 um, 1 micron penetration depth), as well as the ultraviolet excimer lasers from 193 nm to 308 nm have been shown to be capable of ablating biological tissues with minimal thermal damage to the remaining structures. The size of the thermal damage depends on the penetration depth of the specific wavelength and pulse duration: the shorter these parameters, the smaller the zone of thermal damage. Since ablation is a threshold effect, the low energy density at the wings of a tapered laser beam profile may not reach the amount necessary to cause ablation, but only heat this part of the irradiation site, contributing to thermal damage. A homogeneous cross-sectional energy distribution is therefore highly desirous in order to reduce the lateral size of the thermal damage, which is one of the stimuli for undesired scarring and delayed wound healing.

Reduction of thermal damage by limiting the laser pulse duration to the thermal relaxation time has been proposed before by Wolbarsht. The thermal relaxation time has been connected to the penetration depth of the specific laser wavelength by defining it as that time, during which the major portion of the laser energy which is absorbed in the penetration depth, diffuses by heat conduction into a heat diffusion zone—which is proportional to the zone of thermal damage—of the same size as said penetration depth. This has two major inconveniences. First, in the case of the Holmium laser, where the penetration depth (in water) is about 300 um, the allowable maximal laser pulse duration becomes 156 milliseconds, which would result in a relatively large lateral heat diffusion zone of 300 microns. Second, in the case of the Erbium:YAG laser with a penetration depth of 1 micron, it limits the maximal pulse duration to 1.7 microseconds. New considerations are necessary to select more practical pulse durations and to allow zones of heat diffusion which are better adapted to the specific microsurgical procedure.

The Erbium:YAG laser energy can be transmitted through zirconium fluoride optical fibers. These fibers are relatively fragile, and the fiber output end is often damaged during tissue ablation. Provisions have to be taken to avoid the contact of this fiber with biological tissue. The energy of the 193 nm excimer laser can not be transmitted through optical fibers, and articulated arms have to be used to direct the laser beam into a probe.

The small penetration depth of mid-infrared and ultraviolet lasers, which causes the high precision in tissue ablation, inherently limits the amount of ablated tissue and the efficiency of such procedures. It is therefore advantageous to increase the diameter of the irradiated area by using bundles of optical fibers. Laser energy delivery in an annular pattern with a coaxial canal has been proposed before by Berlin in U.S. Pat. No. 4,846,172 and by Davies in U.S. Pat. No. 4,819,632. These patents teach arranging multiple optical fibers in a ring-like pattern and surrounding a central tube. These systems have the disadvantage of needing a large number of small and densely packed fibers to approximate a regular annular pattern, which, in cases involving a short penetration depth of the wavelength, will always consist of multiple spots rather than a homogeneous annulus. In addition, the holding fixture for such a fiber bundle increases the outer diameter of the probe by an undesired amount beyond the diameter of the annulus formed by the laser energy.

Single pulses of mid-infrared lasers are capable of evaporating water and tissue depths in excess of the optical penetration depth, provided the pulse duration and power density are long and high enough to induce a phase change in said penetration depth in a time $t_v$, which is shorter than the pulse duration $t_p$. Later portions of such pulses will then be transmitted through the vapor, which was produced by the earlier portions of the pulse. In conclusion, the laser energy of all mid-infrared lasers can travel a considerable distance beyond the output surface of any probe which is submersed in water or brought in contact with the tissue.

SUMMARY OF THE INVENTION

It is therefore, one of the principal objects of the present invention to provide an apparatus for performing endolaser microsurgery that is used in conjunction with a suitable laser delivery system for ablating tissues, for aspirating the ablated tissue debris and/or fluids, for irrigation, and as an instrument channel using the same instrument, which is particularly applicable in eye surgery for glaucoma, vitreous, and cataract surgery, in orthopedics for back, knee and joint surgery, and for brain surgery.

Another object of the present invention is to provide a probe for use in microsurgery that provides safe and effective delivery of the laser energy to a very limited and specific area and to provide a homogeneous energy distribution to reduce the lateral tissue damage.

A further object of the present invention is to provide a probe for use in microsurgery that controls the shape of the delivered laser beam.

A still further object of the present invention is to provide means for coupling the laser energy delivery system to the probe/aspiration means.

Another object of the present invention is to provide the means to limit the lateral zone of thermal damage according to the specific microsurgical procedure and to control the ablation depth.

Various additional objects and advantages of the present invention will become apparent from the following description, with reference to the accompanying drawings.

BRIEF DESCRIPTION OF THE DRAWINGS

FIG. 4 is a partial cross-sectional and side elevational view of one embodiment of the probe;

FIG. 4A is a cross-sectional view, taken on line 4A—4A of FIG. 4;

FIG. 5 is a partial cross-sectional and side elevational view of another embodiment of the probe;

FIG. 5A is a cross-sectional view taken on line 5A—5A of FIG. 5;

FIG. 6 is a partial cross-sectional and fragmentary side elevational view of another embodiment of the probe;

FIG. 6A is a cross-sectional view taken on line 6A—6A of FIG. 6;

FIG. 7 is a partial cross-sectional and side elevational view of another embodiment of the probe;

FIG. 7A is a cross-sectional view taken on 7A—7A of FIG. 7;

DETAILED DESCRIPTION OF THE PREFERRED EMBODIMENT

The present invention suggests the use of lasers, the wavelength of which are highly absorbed by the tissue to be ablated, so that the maximum penetration depth is limited to 0.2–0.3 mm. Typically such wavelength regions are in the mid-infrared portion of the spectrum from 1.4–11 um, and in the ultraviolet portion from 190–350 um. The typical lasers are Thulium, Holmium, Erbium:YAG, HF, DF, CO and $CO_2$ lasers in the mid-infrared, and excimer lasers in the ultraviolet region.

The present invention further and most important suggests to concentrate the laser power per area of irradiated tissue such, that the time $t_v$ necessary for the vaporization of a layer of the size of the penetration depth d is so short that the absorbed energy diffuses by heat conduction out of the irradiated area into a zone of width z which is substantially smaller than the radius r of said area: With K being the thermal diffusivity ($1.44 \times 10^{-3} cm^2 S^{-1}$ for water), the heat diffuses into a width $z = \sqrt{(K \cdot t_v)}$. For most surgical procedures, a width z, which is, e.g. typically 1 to 2 orders of magnitude smaller than the radius r of the ablated hole, can be accepted. With z being therefore set to be negligibly smaller than r, the vaporization time becomes $t_v = z^2/K$, and the minimum power density p (in watts per $cm^2$) to achieve vaporization of the layer of the penetration depth d within this time $t_v$ becomes $p = K \cdot (d+z) \cdot (L + C \cdot T)/z^2$, where L is the latent heat of vaporization in $J/cm^3$, C the specific heat in $J/cm^3/$degreesC, T the temperature increase from room (or body) temperature to the vaporization temperature. (For water, $L + C \cdot T$ is approximately 2.5 $kJ/cm^3$). The pulse duration $t_p$ can be longer than $t_v$, because after initiating the vaporization process, the heat diffusion is no longer effective. The longer the pulse duration $t_p$, the deeper the tissue ablation. The ablation depth can therefore be controlled by controlling the pulse duration.

Because of the high absorption and small penetration depth, the volume of the evaporated or ablated mass per pulse is relatively limited. This invention therefore proposes the use of a probe, which is able to deliver the laser beam to an area of tissue which is significantly larger than the area of the optical fiber able to transmit the laser pulse, and which allows the aspiration of the ablated material, and in which the outer diameter of the probe is typically 1 to 5 mm.

Figure 1:
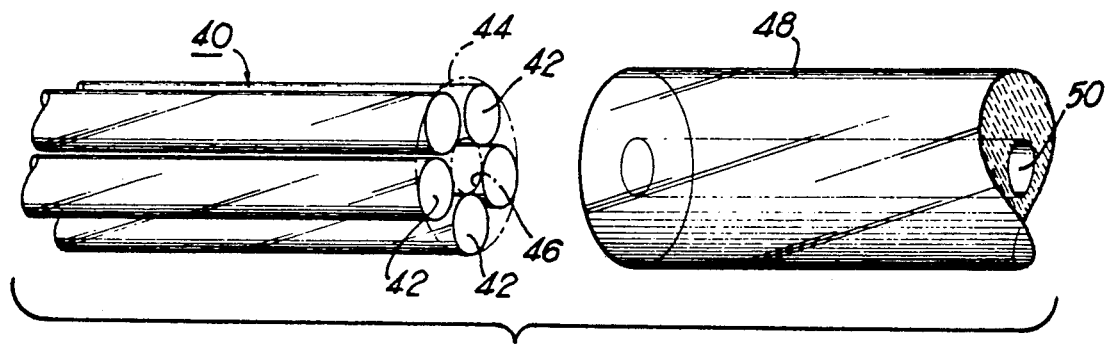
FIG. 1 is a partial perspective and side elevational view of one embodiment of the coupling of the laser delivery means and the probe.

Detailed views of the operative portions of the probe and several embodiments thereof are illustrated in FIGS. 1 through 9C. FIG. 1 illustrates a laser delivery means 40 comprising a bundle of optical fibers 42 contained within a suitable housing 44. A central passageway 46 is maintained for aspiration of ablated material. The fibers are coupled to a suitable laser delivery system (not shown), which is coupled through a suitable means (not shown) to a tubular member 48. As shown in FIGS. 1 and 4, the member 48, preferentially of sapphire, also contains a central passageway 50, which is coaxially aligned with passageway 46. Sapphire is the preferred material for the tube due to its superior laser transmission properties, high mechanical strength, and high melting point, although other suitable materials having like qualities may be used.

Figure 2:
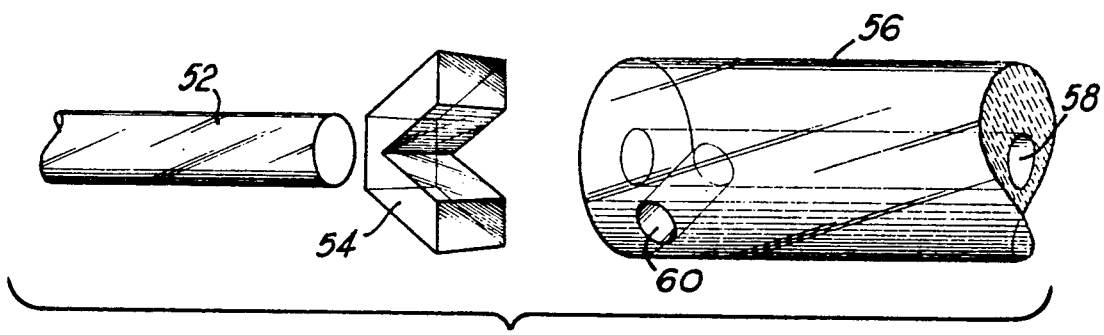
FIG. 2 is a partial perspective and side elevational view of an alternate embodiment of coupling the laser delivery means to the probe.
Figure 3:
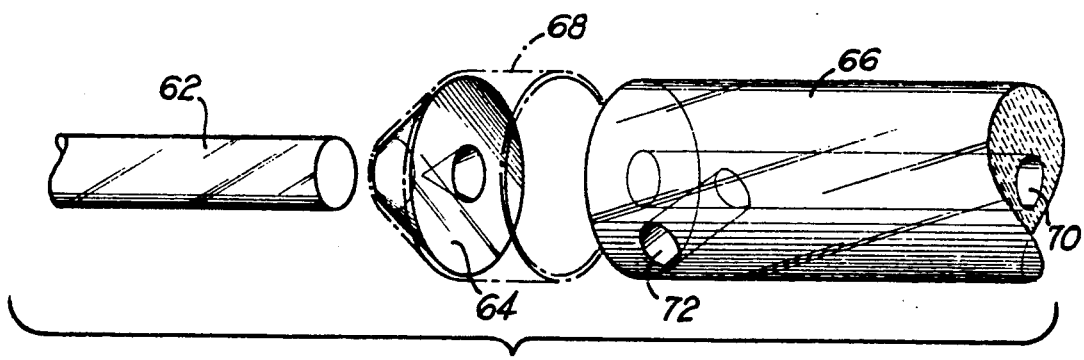
FIG. 3 is a partial perspective and side elevational view of another embodiment of the coupling of the laser delivery means to the probe.

FIGS. 2 and 3 illustrate alternate embodiments of delivering the laser energy to the sapphire tube. In FIG. 2, a single optical fiber 52 delivers the laser energy to a sapphire prism (which is shown in perspective view for clarity) which splits the beam into two or more components for transmission into the sapphire tube 56. Coupling of the prism to the tube 56 is accomplished in any suitable manner, such as with a high temperature adhesive or a suitable tubular sleeve (not shown). Tube 56 also contains a central passageway 58 for aspiration of ablated material and may also include a secondary, offset passageway 60 for irrigation and/or aspiration purposes.

A third embodiment, shown in FIG. 3, couples the optical fiber 62 to a sapphire cone 64, which diverts the laser energy to the sapphire tube 66. A suitable connecting sleeve 68, or similar means, couples the cone 64 to the tube 66. A central aspiration passageway 70 is provided through tube 66 along with a secondary offset passageway 72 which communicates with passageway 70 similar to that shown in FIG. 2 for irrigation or aspiration.

A central theme of the present application is the use of a probe, typically comprising a relatively thick-walled tube of approximately 10 to 30 millimeters in length and a diameter of approximately 1–5 millimeters. Certain required characteristics for the probe include:

a) mechanical rigidity, so that it does not break or fracture upon its manipulations inside the eye or other organ;

b) transmission of laser energy within its walls;

c) the probe is unaffected by the laser interaction with the tissue; and d) the aspiration of evaporated or ablated tissue through a central passageway.

Thus, the probe is typically a hollow tube comprised of an optical material able to transmit laser wavelengths which are highly absorbed by water. The cylindrical tube wall has sufficient thickness to transmit sufficient laser energy to ablate the tissue. The central cylindrical passageway has sufficient diameter to aspirate evaporated or ablated material or fragments thereof. A suitable aspiration system, known in the art, is connected to the central passageway or secondary passageway in any suitable manner.

For certain applications, depending on the laser delivery system utilized, specialized probe design is required. When combined with a Holmium laser (2.1 micron wavelength, penetration in water 300 microns) the laser light is reflected from the inner and outer surfaces of the tube by total reflection, thus the probe can be that illustrated in FIGS. 1 through 4.

With the use of the Erbium laser (2.94 micron wavelength, penetration in water 1 micron), the tube's walls must be protected from contact with water or any water containing material by a special reflective coating or a cladding, or by additional metal tubes with an airspace between the tube and the core. Such specialized probes are illustrated in FIGS. 5 through 7A.

FIGS. 5 and 5A illustrate an embodiment of a probe 78 with a sapphire tube 80 having a central passageway 82 in which the tube 80 and passageway 82 are surrounded by a reflective coating or a cladding material 84 having a low index of refraction.

FIGS. 6 and 6A illustrate an embodiment of a probe 88 having a sapphire tube 90 with a central passageway 92. The sapphire tube 90 and the central passageway 92 are surrounded by a suitable metallic tube 94 with an airspace or void 96 therebetween, for total reflection of the beam.

FIGS. 7 and 7A illustrate another modification wherein the probe 98, comprised of a bundle of optical fibers 100 with a central passageway 101, all are contained within or between two coaxial tubes 102 and 103 which can be metallic tubes, sapphire tubes, or other suitable material. The probe 98 contains a sapphire window 104 for transmission of the laser light and for sealing the distal end of the probe, the window having a central aspiration passageway 106.

Since the laser wavelengths used have only a relatively small penetration depth of a few microns in most ocular tissues, only thin layers can be ablated per laser pulse. By delivering the laser beam through an annular surface, as described hereinabove, which is approximately an order of magnitude larger than the end surface or diameter of the optical fibers used, an increased volume of tissue can be ablated per pulse. This, when combined with an aspiration canal in a probe of a minimal outer diameter, provides for the laser delivery system to be utilized more safely and efficiently than has previously been accomplished.

Figure 8A:
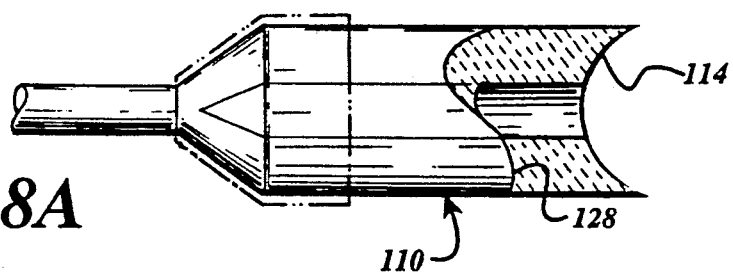
FIG. 8A is a partial cross-sectional view of an embodiment of the probe to diverge the laser beam.
Figure 8B:
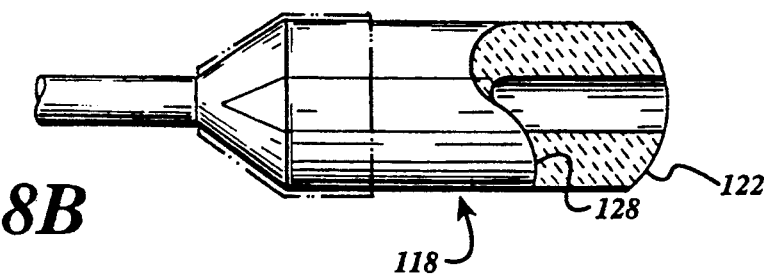
FIG. 8B is a partial cross-sectional view of an embodiment of the probe to converge the laser beam.
Figure 9A:
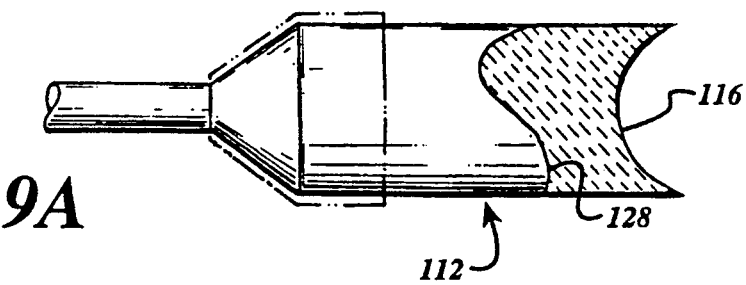
FIG. 9A is a partial cross-sectional view of an embodiment of the probe without central canal to diverge the laser beam.
Figure 9B:
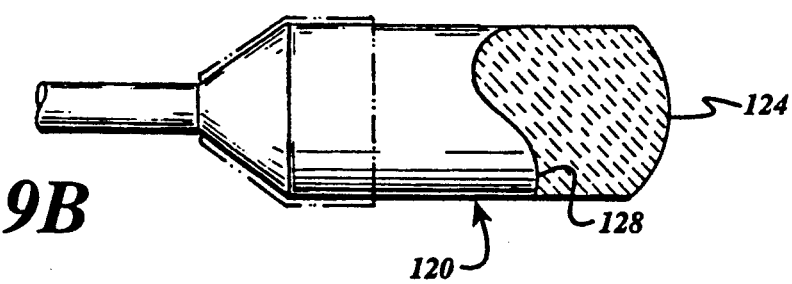
FIG. 9B is a partial cross-sectional view of another embodiment of the probe without central canal to converge the laser beam.
Figure 9C:
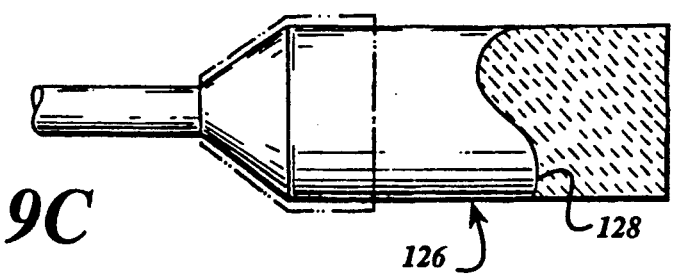
FIG. 9C is a partial cross-sectional view of another embodiment of the probe without central canal.

By using a pulse power and pulse duration high and long enough to evaporate an amount of tissue several times the penetration depth of the wavelength during one pulse, the laser light will exit the optical material of the probe and be transmitted through water vapor and/or gaseous debris before reaching the tissue. It is, therefore, desirable in certain cases to diverge the laser beam in order to dissipate the laser energy and to limit tissue ablation to the immediate neighborhood of the tip by having a concave output surface of the probe, as shown in FIGS. 8A and 9A by probes 110 and 112 with concave outer surfaces 114 and 116, respectively. Or, it may be desirable in certain cases to focus the output beam to concentrate the laser energy into a greater depth by having a convex output surface of the probe, as shown in FIGS. 8B and 9B by probes 118 and 120 with convex outer surfaces 122 and 124, respectively.

In cases, where aspiration and infusion are not necessarily combined with the tip of the probe (general surgery), and where it is desirable to irradiate a relatively large surface (up to 5 mm diameter) of tissue by means of several optical fibers, a solid rod of suitable material, as shown by probes 112, 120 and 126 (FIGS. 9A, B and C, respectively) preferably sapphire, can be used to provide a homogeneous energy distribution at the output by producing multiple reflections of the beam at the cylindrical wall. This is accomplished as described hereinabove, either with a coating, cladding, or sealed air space, a coating 128 being shown for illustrative purposes. Focusing or diverging of the beam is accomplished by having a convex or concave output surface. The same beam controlling technique (focusing or diverging by a convex or concave output surface of the probe) is also useful when other lasers are used, such as the Holmium:YAG, Thulium, and others, having wavelengths that are less absorbed than the Erbium:YAG laser wavelength.

The invention is useful for several procedures in ophthalmic surgery, for example, as a substitute for ultrasonic phacoemulsification in cataract surgery, for vitreous surgery, and for the creation of a new drainage fistula through the sclera in glaucoma surgery. The irrigation necessary in closed-eye surgery can be combined with the invention using common irrigation and aspiration means. The central canal can be used for aspiration and/or irrigation. The invention can also be used in other surgical procedures, for example in lithotripsy (removal of gallstones and kidney stones), in angioplasty (removal of atherosclerotic plaques), in orthopedic surgery for the partial removal of soft tissues in the joints and in herniated discs, where the central canal of the invention can be used as an instrument channel and for carrying a guide-wire (angioplasty), or for brain surgery.

Thus, the invention contemplates the following:

Wavelengths which are highly absorbed by the water and collagen, so that the penetration depth is smaller than typically 0.5 mm. The two wavelength regions are: 1.4 to 11 microns, and below 350 nm.

Power densities (in $W/cm^2$) sufficiently high to rapidly vaporize one penetration depth, so that the energy lost by heat conduction diffuses only into an area which is insignificantly larger than the irradiated and ablated area, thus reducing the amount of scarring and damage to adjacent structures.

Controlling the pulse duration to control the ablation depth.

Delivering such laser power through one or several optical fibers, the end or ends of which are introduced into a metal tube, the end of the metal tube being sealed with a sapphire window or any other material transmitting sufficient laser power, and with the window brought in contact with the tissue to be ablated.

Delivering such laser power through an articulated arm, at the end of which the beam is focused into a metal tube, the end of the metal tube being sealed with a beam transmitting window, which is brought in contact with the tissue to be ablated.

Possible lasers to be used are: the solid state lasers Erbium:YAG at 2.94 um, Erbium:YSGG at 2.79 um, Holmium:YAG at 2.1 um, Thulium:YAG at 1.96 um, the chemical lasers Hydrogen Fluoride at 2.7–3.0 um, and Deuterium Fluoride at 3.7–4.1 um, the gas lasers Carbon Monoxide at 5.3–5.7 um, and Carbon Dioxide at 10.6 um, and the excimer lasers Argon Fluoride at 193 nm, Krypton Fluoride at 248 nm, and Xenon Chloride at 308 nm.

Thus, while an embodiment and modifications thereof of an apparatus, probe, and method of endolaser microsurgery have been disclosed, illustrated, and described in detail herein, various additional changes and modifications may be made without departing from the scope of the present invention.

I claim:

1. A probe for performing endolaser microsurgery and ablating tissues in which said probe is connected to a laser delivery system for delivering pulsed laser power, said system having an optical fiber delivery means with an end surface abutting said probe for conducting said power, said probe comprising a walled tubular member for guiding the laser power through said walls by way of providing multiple reflections at the cylindrical surfaces of said walls and including a central canal through said tubular member for aspiration of liquids and ablated tissue debris and also for use in irrigation and as an instrument channel.

2. A probe as defined in claim 1 in which said tubular member is composed of sapphire having an outer diameter of one to five millimeters.

3. A probe as defined in claim 1 in which said tubular member includes inner and outer cylindrical surfaces with a reflective coating surrounding said surfaces for reflecting the laser power therewithin.

4. A probe as defined in claim 1 in which said tubular member includes inner and outer cylindrical surfaces with a cladding surrounding said surfaces for total reflection of said laser power therewithin.

5. A probe as defined in claim 1 in which said tubular member includes coaxial metal tubes surrounding said inner and outer cylindrical surfaces and including a sealed air space therebetween for total reflection.

6. A probe as defined in claim 1 in which said tubular member includes a convex output surface for focusing the laser power.

7. A probe as defined in claim 1 in which said tubular member includes a concave output surface to diverge the laser power.

8. A probe as defined in claim 1 in which said laser delivery system includes an articulated arm with mirrors and including a beam splitting reflecting prism coupled between the output of said articulated arm and said probe.

9. A probe as defined in claim 1 in which said laser delivery system includes an articulated arm with mirrors and including a conical reflecting prism coupled between the output of said articulated arm and said probe, and said tubular member includes a secondary passageway communicating with said central canal for aspiration and irrigation.

10. An apparatus for controlled tissue ablation including a laser system generating a laser wavelength which penetrates less than 300 um in water and collagen containing biological tissues, and having a laser beam delivery system for delivering sufficient laser power density p to evaporate a depth of tissue substantially equal to the penetration depth d of said wavelength in a time $t_v$, which is sufficiently short, so that the width z of the zone, into which the absorbed energy dissipates by heat conduction, is, by a pre-determined amount, smaller than the radius r of the zone irradiated by the laser beam.

11. An apparatus for controlled tissue ablation as in claim 10, where the laser power density is at least $p = K \cdot (d+z) \cdot (L + C \cdot T)/z^2$, and wherein z is smaller than 0.1 times the radius r of the irradiated area, and is the width of the zone in which absorbed energy dissipates by heat conduction during the evaporation process, K is the thermal diffusivity in $cm^2 s^{-1}$, d is the optical penetration depth of the laser beam, L is the latent heat of vaporization in $J/cm^3$/degrees C., and T is the temperature increase from body to vaporization temperature in degrees C.

12. An apparatus for controlled tissue ablation as in claim 10, where the laser pulse duration $t_p$ can be controlled to control the ablation depth.

13. A probe for performing endolaser microsurgery and for uniformly ablating tissues in which said probe is connected to a laser delivery system for delivering pulsed laser power, said system having optical fiber delivery means with an end surface abutting said probe for conducting said laser power, said probe comprising a solid cylindrical member of a diameter larger than the end surface of the optical fiber to increase the irradiated tissue area, and for homogenizing the cross-sectional laser power distribution therewithin by way of providing multiple reflections at the cylindrical surface and in which the laser delivery system includes a laser apparatus generating laser power having a penetration depth of less than 300 microns in water and collagen containing biological tissues, for delivering sufficient pulse power at the output of said probe to evaporate tissue and the like up to said penetration depth at a rate such that no significant amount of energy diffuses through heat conduction outside a diameter which is smaller than 1.1 times the diameter of the laser irradiated area, and which pulse duration of said laser apparatus can be varied to control the ablation depth.

14. A probe as defined in claim 13, in which said cylindrical member includes a cylindrical surface with a cladding surrounding said cylindrical surface for total reflection of said laser power.

15. A probe as defined in claim 13 in which said cylindrical member includes a coaxial metal tube surrounding said cylindrical surface and including a sealed air space therebetween for total reflection of said laser power.

16. A probe as defined in claim 13 in which said cylindrical member includes a convex output surface for focusing said laser power.

17. A probe as defined in claim 13 in which said cylindrical member includes a concave output surface for diverging said laser power.

18. A probe as defined in claim 13 in which said laser delivery system includes an articulated arm with mirrors connected to said cylindrical member.

19. A probe as defined in claim 13 in which said cylindrical member is composed of sapphire.

20. A probe as defined in claim 13 in which said cylindrical member includes a cylindrical surface with a reflective coating surrounding said cylindrical surface for reflecting said laser power.

* * * * *